United States Patent [19]

Surani et al.

[11] Patent Number: 5,545,807
[45] Date of Patent: Aug. 13, 1996

[54] PRODUCTION OF ANTIBODIES FROM TRANSGENIC ANIMALS

[75] Inventors: Azim M. Surani; Michael S. Neuberger; Marianne Bruggemann, all of Cambridge, Great Britain

[73] Assignees: The Babraham Institute, Cambridge, United Kingdom; Medical Research Council, London, United Kingdom

[21] Appl. No.: 286,399

[22] Filed: Aug. 5, 1994

Related U.S. Application Data

[63] Continuation of Ser. No. 671,849, filed as PCT/GB90/01207, Oct. 12, 1989 published as WO90/04036, Apr. 19, 1990, abandoned.

[30] Foreign Application Priority Data

Oct. 12, 1988 [GB] United Kingdom .................. 8823869

[51] Int. Cl.$^6$ .................. C12N 15/00; A61K 39/00; C07K 16/00; C12P 21/08
[52] U.S. Cl. .................. 800/2; 424/184.1; 530/387.3; 530/388.15; 530/387.1; 435/172.3; 435/172.2; 536/23.53
[58] Field of Search .................. 800/2; 514/44; 536/23.53

[56] References Cited

PUBLICATIONS

Yamamura et al PNAS 83: 2152, 1986.
Alt et al. TIG 1:1, 1985 (Aug.).
Berma et al. EMBO J 7(3): 727 198.
Goodhardt et al PNAS 84, 4229, 1987.
Ritchie et al Nature 312: 517 1984.
Goodnow et al Nature 334: 676, 1988.
Bruggeman et al J. Exp. Med. 166: 1351, 1907.
Scangos et al T1G 24: 285, 1987.
Bucchini et al, "Rearrangement of a chicken immunoglobulin gene occurs in the lymphoid lineage of mice", Nature, vol. 326, Mar. 1987, pp. 409–411.
Bruggemann et al, "A repertoire of monoclonal antibodies with human heavy chains from transgenic mice", Proc. Natl. Acad. Sci. USA, vol. 86, Sep. 1989, pp. 6709–6713.

*Primary Examiner*—Suzanne E. Ziska
*Attorney, Agent, or Firm*—Cushman Darby and Cushman

[57] ABSTRACT

Chimaeric or wholly foreign immunoglobulin is obtained from cells or body fluid of a transgenic animal which has had inserted into its germline genetic material that encodes for at least part of an immunoglobulin, of foreign origin or that can rearrange to encode a repertoire of immunoglobulins, i.e. derived from a different animal source. For example, wholly human immunoglobulins may be produced from a transgenic mouse, possibly in response to an immunogen subsequently introduced to the mouse.

5 Claims, 8 Drawing Sheets

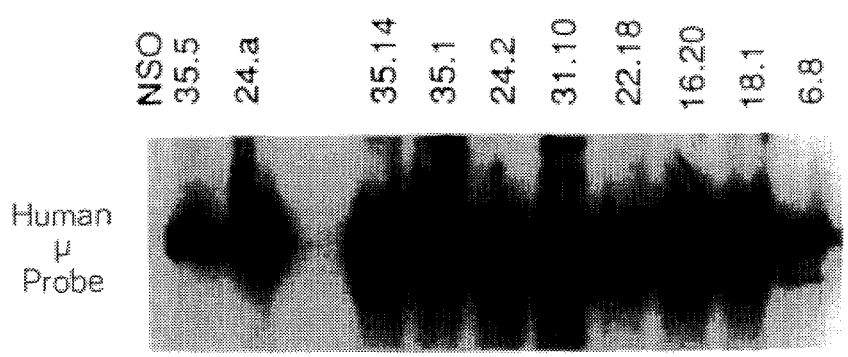
FIG. 3A Human μ Probe
FIG. 3B V$_H$186 Probe
FIG. 3C V$_H$26 Probe

MEAN CHANNEL = 25.
(25. WITH OVERFLOW)

MEAN CHANNEL = 53.
(53. WITH OVERFLOW)

MEAN CHANNEL = 26.
(26. WITH OVERFLOW)

PRODUCTION OF ANTIBODIES FROM TRANSGENIC ANIMALS

This is a continuation of application Ser. No. 07/671,849, filed as PCT/GB90/01207, Oct. 12, 1989, published as WO90/04036, Apr. 19, 1990, now abandoned.

FIELD OF INVENTION

This invention concerns the production of antibodies (or immunoglobulins).

SUMMARY OF THE INVENTION

According to one aspect of the present invention there is provided a method of producing an immunoglobulin, comprising obtaining immunoglobulin from cells or body fluid of a transgenic animal which has had inserted into its germline genetic material that encodes for at least part of an immunoglobulin of foreign origin or that can rearrange to encode a repertoire of immunoglobulins.

An immunoglobulin of foreign origin means an immunoglobulin derived from a different animal source. For example where the transgenic animal is a mouse, the inserted genetic material is of non-mouse, e.g. human, origin.

The inserted genetic material may be produced from an animal source, or may be produced synthetically. The material may code for at least part of a known immunoglobulin or may be modified to code for at least part of an altered immunoglobulin. Suitable techniques for these processes are well known.

The inserted genetic material may be expressed in the transgenic animal, resulting in production of an immunoglobulin derived at least in part from the inserted material. It is found the genetic material is rearranged in the transgenic animal, so that a repertoire of immunoglobulins with part or parts derived from inserted genetic material may be produced even if the inserted genetic material is incorporated in the germline in the wrong position or with the wrong geometry. Depending on the nature of the inserted material, the animal may produce a chimaeric immunoglobulin, e.g. of mixed mouse/human origin, where the genetic material of foreign origin encodes only part of the immunoglobulin, or the animal may produce an entirely foreign immunoglobulin, e.g. of wholly human origin, where the genetic material of foreign origin encodes an entire immunoglobulin. Potentially therapeutically useful immunoglobulins suitable for use with humans thus may be produced by use of the invention.

Polyclonal antisera may be produced from the transgenic animal following immunisation. Alternatively, monoclonal antibodies may be produced from the transgenic animal, eg by fusing spleen cells from the animal with myeloma cells and screening the resulting hybridomas to select those producing the desired antibody. Suitable techniques for such processes are well known to those skilled in the art.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of an immunoglobulin of foreign origin into a gene of a mammal coding for a milk protein and then introducing the gene to a fertilised egg of the mammal, eg by injection, the egg may develop into an adult female mammal producing milk containing immunoglobulin derived at least in part from the inserted genetic material. The desired antibody may then be harvested from the milk. Suitable techniques for carrying out such processes are known to those skilled in the art.

Another possibility involves removal from the animal of immunoglobulin-producing cells generated by the animal after insertion of genetic material, followed by in vitro selection of cells producing an immunoglobulin of interest. The immunoglobulin can then be produced in vitro from the selected cells in known manner.

It has been found that a transgenic animal can produce chimaeric or foreign immunoglobulin (derived from inserted genetic material) in response to an immunogen subsequently introduced to the animal. Accordingly, by introducing foreign, eg human, genetic material encoding for substantially the entire species specific regions of an immunoglobulin it may be possible to stimulate the animal to produce foreign immunoglobulin to any antigen introduced to the animal. The transgenic animal could thus provide a highly useful, convenient and valuable source of human immunoglobulins to a large range of antigens.

It is though that it may be important for the inserted genetic material to be integrated in proximity genome for successful rearrangement. The inserted genetic material may thus be in the form of DNA cloned into prokaryotic vectors such as plasmids and cosmids. Multiple plasmids or cosmids may also be used, but it is probably necessary for these to integrate in proximity on the genome. It may also prove possible to insert larger DNA fragments by using yeast artifical chromosome vectors (see Burke, D T, Carle, G F and Olson, M V (1987) "Cloning of large segments of exogenous DNA into yeast by means of artifical chromosome vectors" Science, 236, 806–812), or by introduction of chromosome fragments (see Richer, J and Lo, C W (1989) "Introduction of human DNA into mouse eggs by injection of dissected human chromosome fragments" Science 245, 175–177).

The inserted genetic material may be introduced to the host in conventional manner, for example by injection or other procedures into fertilised eggs or embryonic stem cells.

It may be convenient to use a host animal that initially does not carry genetic material encoding immunoglobulin constant regions so that the resulting transgenic animal will use only the inserted foreign genetic material when producing immunoglobulins. This can be achieved either by using a naturally occuring mutant host lacking the relevant genetic material, or by artificially making mutants eg in cell lines ultimately to create a host from which the relevant genetic material has been removed.

Where the host animal carries genetic material encoding immunoglobulin constant regions, the transgenic animal will carry the naturally occuring genetic material and the inserted genetic material and will produce immunoglobulins derived from the naturally occuring genetic material, the inserted genetic material and mixtures of both types of genetic material. In this case the desired immunoglobulin can be obtained by screening hybridomas derived from the transgenic animal, eg by exploiting the phenomenon of allelic exclusion of antibody gene expression or differential chromosome loss.

In a further aspect the present invention produces a transgenic animal, particularly a non-human mammal, which has had inserted into its germline genetic material that encodes for at least part of an immunoglobulin of foreign origin, or that can rearrange to encode a repertoire of immunoglobulins.

The invention also includes within its scope an immunoglobulin produced from a transgenic animal in accordance with the invention or produced by the method of the invention.

In one example, lines of transgenic mice were established, carrying a DNA segment introduced into their germline that contains germline-configuration immunoglobulin VH genes, some of the D segments, and all the JH and Cmu gene segments. One of the VH genes, all the JH segments and the exons encoding the secreted heavy-chain constant region of IgM antibody were of human origin, with the remaining material being of mouse origin. The gene segments undergo productive VH-D-JH joining in the lymphoid tissue of the transgenic mice, with resultant synthesis of human/mouse chimaeric IgM antibody in serum.

Following immunisation, hybridomas have been established by fusion between spleen cells from the transgenic mice with the NSO myeloma. Many of the hybrids secerete human chimaeric IgM monoclonal antibodies. These lines of transgenic mice can therefore be used for the production of chimaeric human antisera or monoclonal antibodies.

Further, the mice make a response following immunisation with human antigens, producing chimeric antibodies to introduced antigen, and this approach should therefore also prove useful for the production of a repertoire of conventional human or chimaeric human antibodies directed against human as well as heterologous antigens, as the transgenic mice will not be tolerant to human antigenic determinants.

In another example, transgenic mice carrying exclusively human VH, D, JH and C mu sequences were produced by injecting into fertilised mouse eggs cosmids containing human VH genes, D segments, J segments and the C mu constant region. Resulting mice produced between 10 and 100 ug/ml antibody containing human mu chains in their serum, with mouse IgM being present at about 200 ug/ml.

The invention will be further described, by way of illustration, in the following Examples which refer to the accompanying drawings, in which:

FIG. 3(A–C) is a Northern blot analysis of cytoplasmic RNA from hybridomas from the transgenic mice;

EXAMPLE 1

The Transgene

Figure 1:
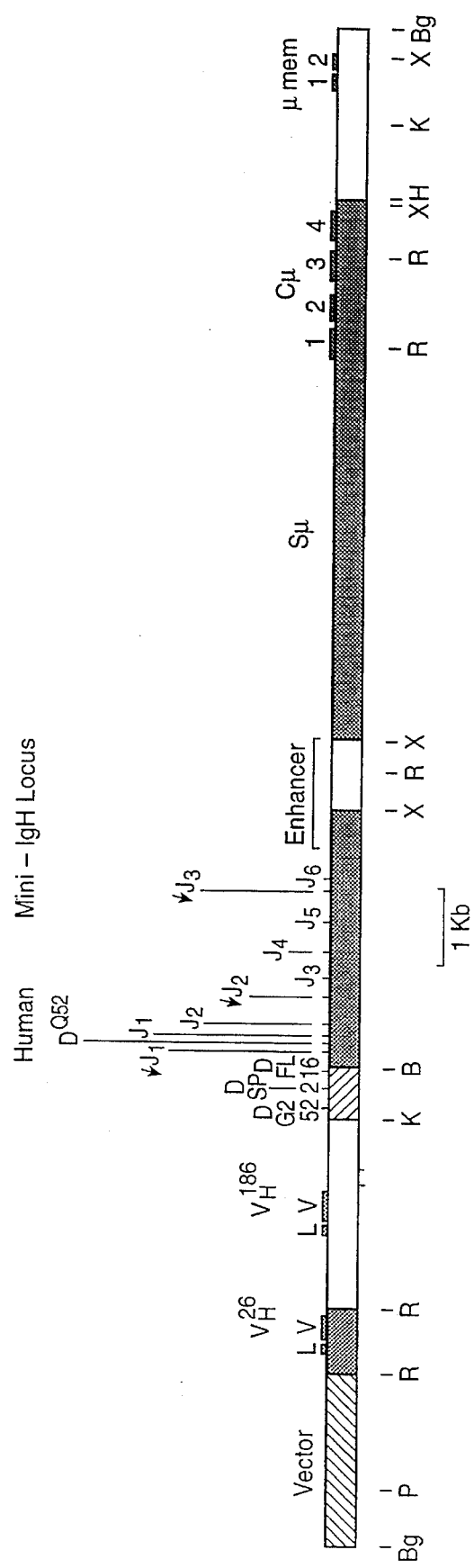
FIG. 1 illustrates the structure of plasmid DNA.

Plasmid DNA with the structure shown in FIG. 1 was injected into mouse eggs. In this Figure human sequences are represented by filled bars; mouse sequences by unfilled bars; vector by cross-hatched bars, and D elements by reverse hatched bars. Restriction endonuclease cleavage sites are abbreviated as follows: Bg, BglII; P,. PvuI; R, EcoRI: K, KpnI; B, BamHI; X, XbaI; H, HindIII.

The provenance of the constituent DNA segments is as follows:

The Vector: The entire "mini-IgH locus" was cloned between the EcoRI and BglII site of a pUC12 derivative that contains BglII linkers cloned into a filled-in NarI site.

The VH genes: There are two VH genes in the mini-locus. The VH26 is of human origin and was obtained as a BglII-EcoRI 0.85 Kb fragment from phage lambda VH26 [Matthyssens & Rabbitts (1980) PNAS 77, 6561–6565]. The VH-186.2 is a germline VH gene from C57BL/6 mice and was obtained as 2.5 Kb SacI-KpnI fragment [Bothwell, Paskind, Reth, Imanishi-Karl, Rajewsky & Baltimore (1981) Cell 24, 625–637].

The D segments: the BALB/c mouse D-Q52 element was obtained as a 221 nt XhoI-SacI fragment. Following cloning between the SacI and SalI sites of M13tg131, site directed mutagenesis with either oligonucleotide
5'-GCGTCACCGTGGTAGCTGCTACCGTAG-TAATAAACACTGTGGTCC or
5'-GCGTCACCGTGGTCGTAACCATAGTAGA-CACTGTGGTGC
was used to create M13tg131 clones carrying D elements related to those of the mouse SP2 and FL16 families, respectively. These D families are found in both mouse and human. Another D element—the human D-Q52—was included within the human JH cluster (see below).

The JH cluster: A 3.5 Kb BglII fragment from human DNA was used that includes the six functional human JH segments, three pseudo JHs as well as the human D-Q52 element [Ravetch et al. (1981) Cell 27, 583–591].

The IgH Enhancers: Part of the human IgH enhancer is included within the BglII fragment containing the JH cluster. A full copy of the mouse enhancer is included within the 1 Kb XbaI fragment.

The Switch region and Cmu region: The 7.5 Kb Xbal fragment of human DNA includes the mu switch region and exons 1 to 4 of the mu heavy-chain constant region. The mu membrane exons and the bulk of the intron between the Cmu4 exon and the CmuM1 membrane exon are provided by a 2.5 Kb HindIII-SphI fragment of the mouse mu CH gene in which the SphI site was converted to a BglII site by use of linkers.

The Transgenic mice

Plasmid DNA was linearised with BglII, purified after electrophoresis in an agarose gel and injected into the male pronucleus of fertilised eggs of C57BL/6J×CBA/Ca mice as previously described [Reik et al. (1987) Eur. J. Immunol. 17, 465–469]. Southern blot analysis of tail DNA revealed that 12 of the 32 mice born carried the mini-locus. Most subsequent work was performed on offspring of three founder mice—HIg 17, 19 and 29 all of which carry a low number (2–5) of copies of the mini-locus.

Serum Assays

Serum of the founder mice was tested by ELISA for the presence of antibody containing antigenic determinants characteristic of human IgM. The unimmunised transgenic mice proved to contain between 10 and 100 ug/ml of chimaeric human IgM in their serum. Immunofluorescence analysis of lymphocytes in peripheral blood also revealed the presence of cells staining with biotinylated species-specific anti-human Ig M antibody and fluorescein-conjugated streptavidin.

Hybridomas from transgenic mice

Transgenic mice were immunised intraperitoneally with either human red blood cells or sheep red blood cells. Spleens were removed at various times after immunisation, fused with the NSO myeloma and hybrids selected in HAT medium. Many of these hybrids made chimaeric human IgM as revealed by ELISA assay.

DNA Rearrangement of the mini-locus

Southern blot analysis of DNA from tissues from the transgenic mice as well as from the hybridomas revealed that there is a high frequency of DNA rearrangements within the mini-Ig locus in the lymphoid tissue of the transgenic mice.

Figure 2:
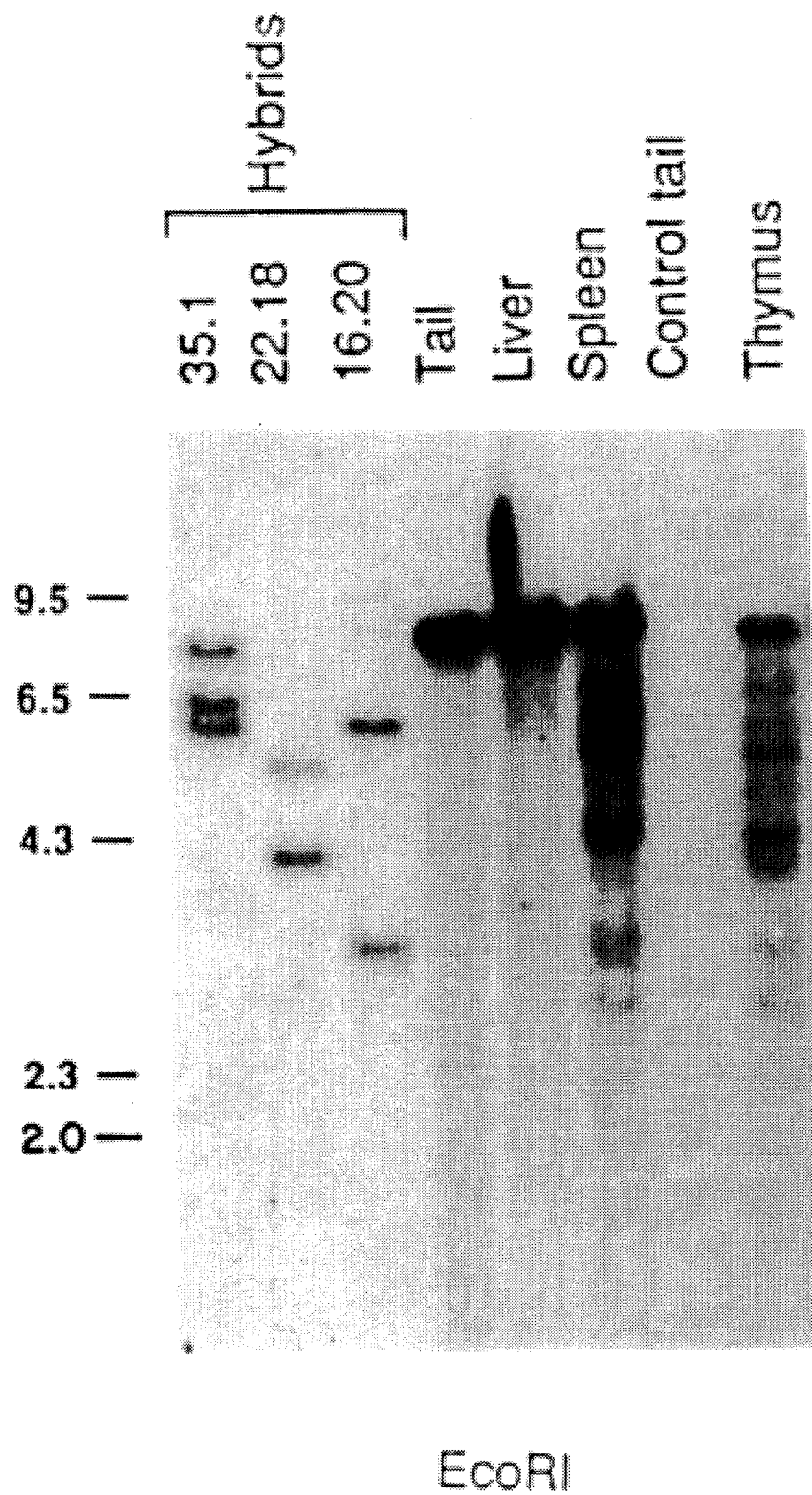
FIG. 2 is a Southern blot analysis of DNA from tissues and from hybridomas derived from transgenic mice with the DNA of FIG. 1 incorporated into the germline.

DNA from tissues or hybridomas established from the transgenic mice was digested with EcoRI and hybridized with a human IgH enhancer probe (BalI-BglII fragment) that hybridizes to the region between the human J6 element and the mouse IgH enhancer in the mini-locus. The result's of Southern blot analysis of the DNA are shown in FIG. 2. The sizes in Kb of marker fragments are given in the Figure.

Transcription of the mini-locus

Cytoplasmic RNA (5 ug) from the NSO fusion partner or from hybridomas from the transgenic mice was probed with human Cmu, human VH26 or mouse VH186 probes The results of Northern blot analysis of the cytoplasmic RNA are shown in FIG. 3(A–C), which reveals that the hybridomas contained mRNA that hybridized with probes for human mu as well as for either or both of the VH26 or VH186 V genes. Thus both the human VH26 and mouse VH186 are able to rearrange and thus create a cell-line that secretes a chimaeric human IgM antibody.

Antibody secretion by hybridomas from the transgenic mice

Figure 4:
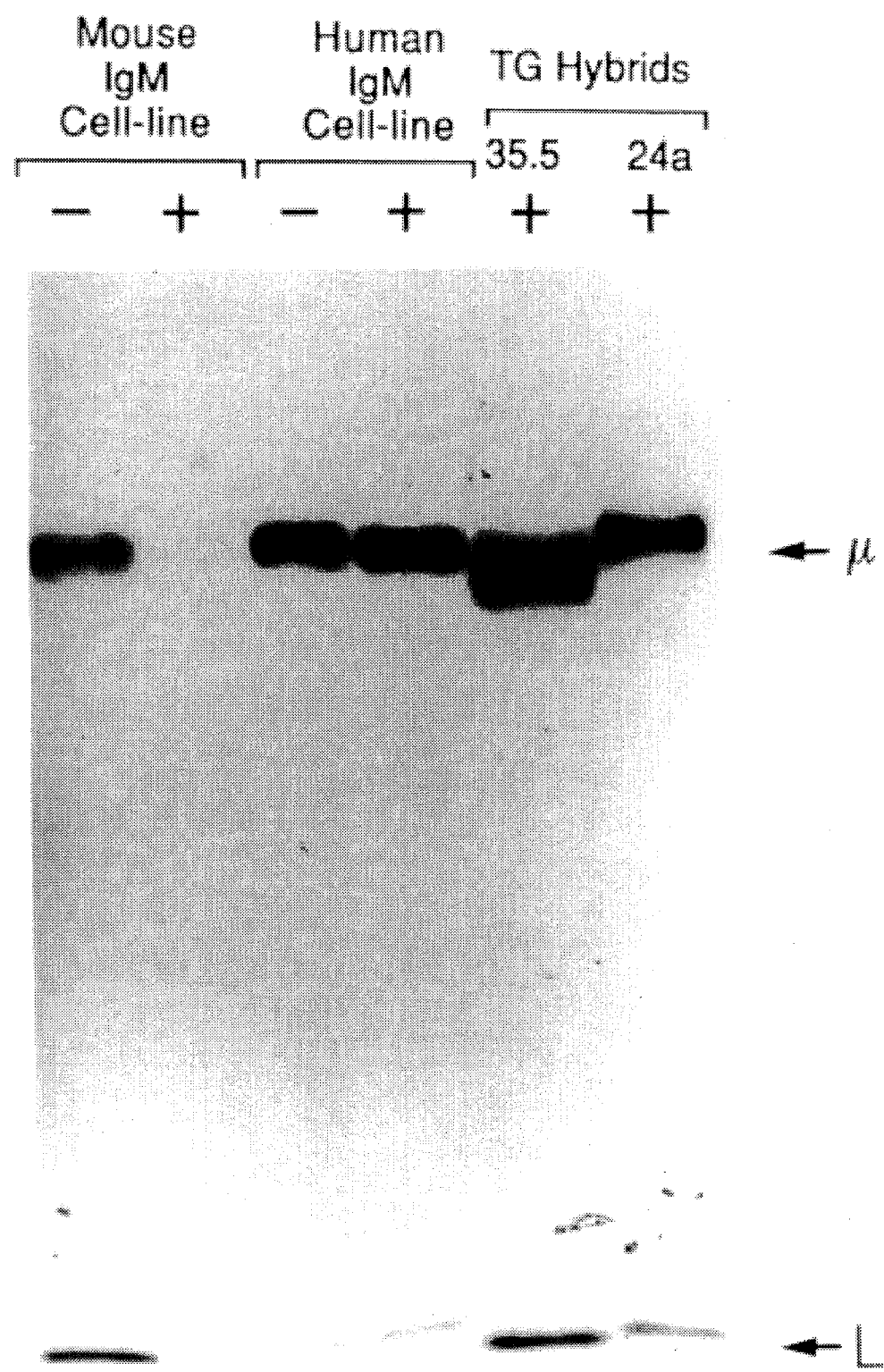
FIG. 4 is an analysis of immunoglobulin secreted by two of the hydridomas established from the transgenic mice.

Protein production by cloned hybridoma cell-lines was analysed by use of biosynthetic labelling with L-[$^{35}$S] methionine and subsequent purification with anti-human mu antiserum. In particular, cells were incubated overnight in medium containing L-[$^{35}$S] methionine and IgM antibody purified from the culture supernatant by immunoprecipitation and an anti-human mu antiserum. The purification from the supernatants of the transgenic hybridomas 35.5 and 24a was performed in the presence of a large excess (50 ug) of non-radioactive, purified mouse monoclonal IgM antibody (B1-8) as indicated by "+" in FIG. 4. As seen using the mouse IgM secreting cell-line, the anti-human mu antiserum cross-reacts with mouse mu but this cross-reaction can be competed by non-radioactive mouse B1-8 IgM antibody—see the four lanes on the left of FIG. 4.

This illustrates that it is possible to establish hybridomas from these transgenic mice that secrete antibodies with different human mu chains.

EXAMPLE 2

Transgenic animals can be created that produce specific antibodies in both their body fluids and external secretions. By way of illustration, this example concerns transgenic mice that carry integrated into their germline the genes encoding the heavy and light chains of an antigen-specific chimaeric human IgA2 antibody.

Figure 5:
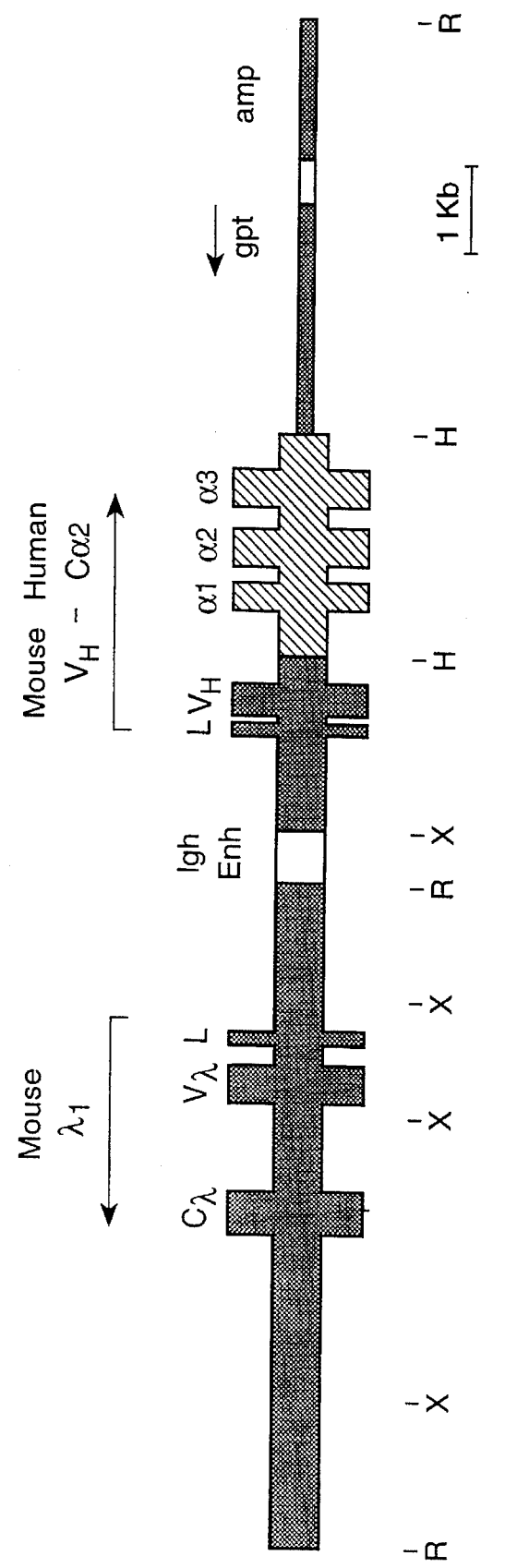
FIG. 5 illustrates the structure of IgA lambda plasmid DNA.

Nine transgenic mouse lines were established that carried germline integrations of the DNA illustrated in FIG. 5. In FIG. 5, the thick filled lines depict mouse Ig DNA, the hatched lines human DNA, open boxes the mouse IgH and SV 40 enhancers, and thin filled lines the pSV2gpt vector. Restriction site abreviations are as in FIG. 1. The plasmid is a derivative of pSV-VNPH alpha 2 described previously [Bruggemann et al, J. Exp. Med (1987) 166, 1351–1361] and contains a 7.4 kb EcoRI fragment including the rearranged lambda 1 gene of the mouse HOPC2020 plasmacytoma [Bernard et al (1978), Cell 15, 1133–1140]. Plasmid DNA was linearised at the PvuI site in the vector and transgenic mice derived as previously described [Reik et al, Eur. F. Immunol (1987) 17, 465–469].

The transgenic IgA 2 lambda antibody has specificity for the hapten 4-hydroxy-3-nitrophenacetyl (NP). Expression of the transgenic antibody was measured by ELISA assay using NP-bovine serum albumin coupled to the plastic plate and developing with a biotinylated anti-human alpha antiserum. Total Ig was measured using anti-mouse Ig coated plastic and developing with biotinylated anti-mouse kappa antiserum. The concentration of chimaeric anti-NP IgA2 was determined in the colostrum, serum and milk from seven transgenic mice and one control mouse, and the resuts are given in Table 1. Colostrum was taken from the mother following hormonal injection within 24 hours of giving birth and milk was taken from the mother when the litter was 13–15 days old; serum was obtained at the same time as milk.

From these data it is clear that transgenic animals can be used for specific antibody production thus allowing large scale production from milk, colostrum, sera, saliva etc as well as allowing the breeding of animals that yield a milk that is dosed with specific beneficial antibodies. It is also clear that the concentration of transgenic antibody is higher in colostrum than in milk. Moreover, the presence of the transgene does not affect the ability of the animal to make a large amount of endogenous antibody. The animals show no signs of being significantly immunodeficient or unhealthy.

EXAMPLE 3

In this example, antigen-specific hybridomas were produced using human mu chains from transgenic mice.

To show that the transgenic mice described in Example 1 can be used to produce antigen-specific antibodies in which the heavy-chain contribution to the antigen-combining site is provided by the transgenic human heavy-chain minilocus, the transgenic mice were immunised with $10^7$ sheep red cells (SRC). Spleen cells were fused 6 days later with the NSO plasmacytoma (Köhler and Milstein, Nature, 256, 495–497, 1975). Cells were plated out in 96-well costar plates such that the expected seeding frequency was 1 hybridoma per well. Human mu positive hybrids were detected in an ELISA using biotinylated anti-human IgM. Antigen-specific hybrids have been identified in haemagglutination using sheep red cells. Wells were chosen that contained antibodies specific for sheep red cells and that contained human mu but neither mouse mu nor mouse gamma heavy chains as determined by ELISA.

To demonstrate that the antibody secreted by the selected hybridomas was indeed a human mu/mouse light chain anti-SRC immunoglobulin, analysis in a fluorescence-activated cell sorter (FACS) was used. For FACS analysis, $10^7$ sheep red cells were incubated with 20 ul culture supernatant for 30 min, washed with phosphate-buffered saline once and further incubated with either biotinylated anti-human mu heavy chain antiserum, biotinylated anti-mouse mu antiserum or biotinylated anti-mouse kappa light chain anti-serum. After 30 min cells were washed as before and incubated with FITC coupled streptavidin. Cells were washed after 30 min and after gentle disruption were ready for the anaylsis.

Results for 3 different hybrids producing IgM directed against the sheep red cell antigen are shown in the FACS histograms of FIGS. 6(A–D), 7(A–C) and 8(A–C), respectively.

Figure 6A:
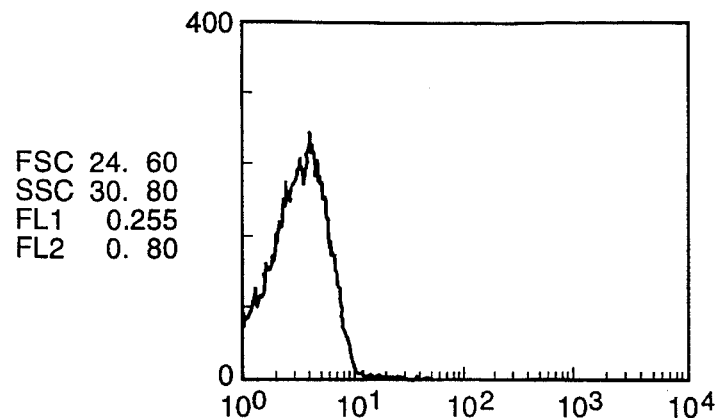
FIG. 6(A–D) is a series of FACS histograms showing fluorescence intensity of a fixed number of cells plotted against cell number.
Figure 6B:
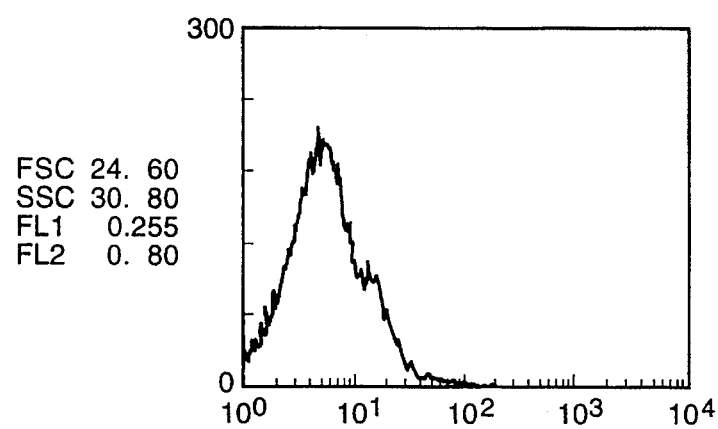
Figure 6C:
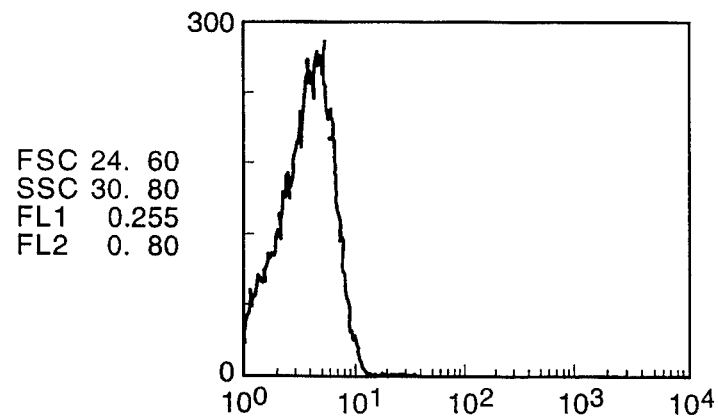
Figure 6D:
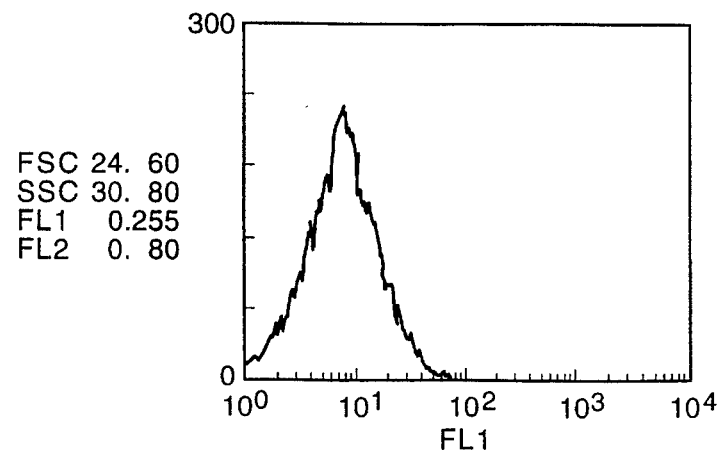
Figure 7A:
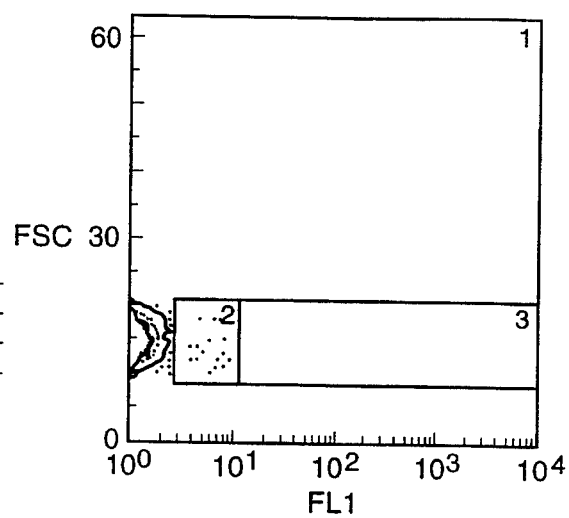
FIG. 7(A–C) is a series of FACS profiles showing fluorescence intensity of a fixed number of cells plotted against scatter, with each dot representing a cell.
Figure 7B:
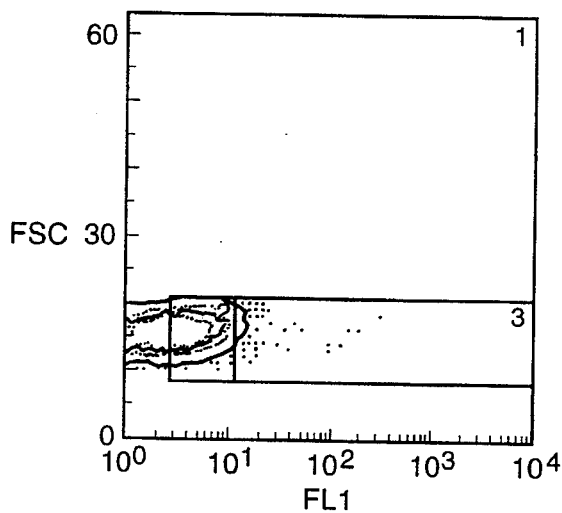
Figure 7C:
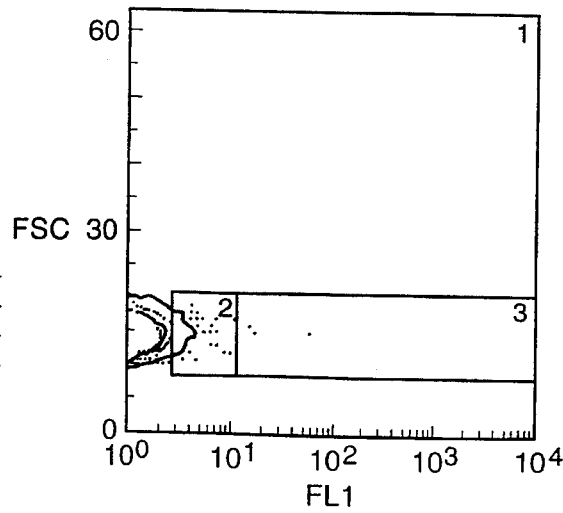
Figure 8A:
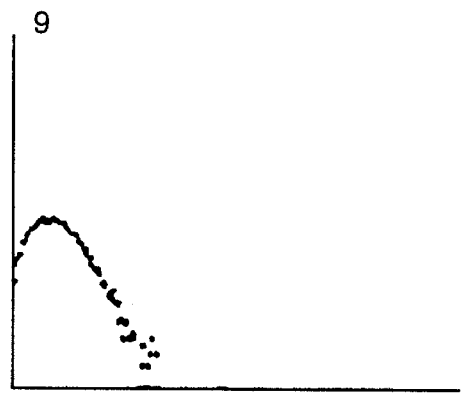
FIG. 8 is a further series of FACS histograms similar to FIG. 6.
Figure 8B:
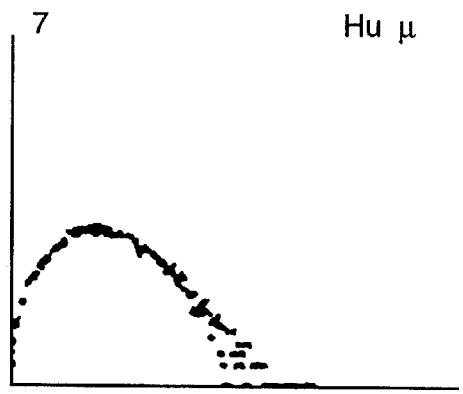
Figure 8C:
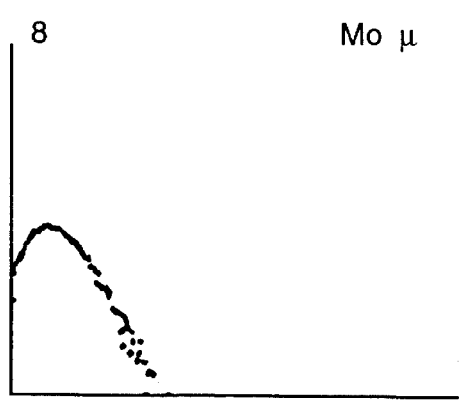

The letters A, B, C and D in these Figures denote different staining. FIGS. 6A, 7A, 8A are results for negative controls using sheep red cells alone, sheep red cells incubated with antibody or sheep red cells incubated with fluorescinated (FITC) second antibody (either anti-human mu anti-mouse mu, anti-mouse kappa). FIGS. 6B, 7B, 8B are results using sheep red cells incubated with hybrid culture supernatant and fluoresceinated (FITC) anti-human mu. FIGS. 6C, 7C, 8C are results using sheep red cells incubated with culture supernatant from the transgenic hybrids and fluoresceinated (FITC) anti-mouse mu. FIG. 6D is results using sheep red cells incubated with hybrid culture supernatant and fluoresceinated (FITC) anti-mouse kappa.

In FIGS. 6(A–D) and 8(A–C) fluorescence intensity of a fixed number of cells is plotted against cell number. In FIG. 7(A–C) fluorescence intensity of a fixed number of cells is plotted against scatter, with each dot representing a cell.

A shift of the profiles to the right (increased fluorescence) denotes a positive stain that can only been seen for antibodies containing human mu heavy chains and mouse kappa light chains but not for antibodies containing mouse mu heavy chains or mouse gamma heavy chains (not shown).

TABLE 1

Antibody in the body fluids of IgA2, lambda 1-mice

| Mouse | IgA2 anti NP Ab | | | Total kappa bearing Ab | |
|---|---|---|---|---|---|
| | Serum | Milk | Colostrum | Milk | Colostrum |
| TG1 | 10 | 0.6 | 2.1 | 960 | 600 |
| TG2 | 6.3 | 0.56 | 1.4 | 1000 | 420 |

TABLE 1-continued

Antibody in the body fluids of IgA2, lambda 1-mice

| Mouse | IgA2 anti NP Ab | | | Total kappa bearing Ab | |
|---|---|---|---|---|---|
| | Serum | Milk | Colostrum | Milk | Colostrum |
| TG3 | 11.3 | 1.3 | ND | 735 | ND |
| TG4 | 7.3 | 0.8 | 1.4 | 780 | 660 |
| TG5 | 30 | 7.6 | 10.0 | 1250 | ND |
| TG6 | 34.6 | 5.0 | 10.0 | 500 | 600 |
| TG7 | 6.3 | 0.64 | 0.93 | 780 | 600 |
| Control | 0 | 0 | 0 | 1136 | 660 |

ND, not determined
All concentration in ug/ml

We claim:

1. A transgenic mouse which has had inserted into its genome DNA comprising human Vh, human Dh, human Jh segments and human mu segments of human immunoglobulins in germline configuration, such that said Vh, Dh, Jh and mu DNA segments in said germline configuration rearrange in said mouse to form a repertoire of immunoglobulins containing portions which correspond to said human DNA segments, and are expressed in said mouse to produce heavy chains, said heavy chains being capable of forming functional heavy chain-light chain immunoglobulins, said immunoglobulins being expressed in an amount allowing for recovery from suitable cells or body fluids of said mouse.

2. A method of producing immunoglobulins to a particular antigen comprising administering said antigen to the transgenic mouse of claim 1, and obtaining said immunoglobulins from the cells or body fluids of said mouse.

3. The method according to claim 2 wherein said immunoglobulins are polyclonal.

4. The method according to claim 2 wherein said immunoglobulins are obtained from the B cells of said mouse.

5. A method for producing a monoclonal antibody comprising immunizing the mouse of claim 1, and isolating the B cells therefrom, fusing said B cells with a suitable myeloma fusion partner to produce hybridomas, culturing said resulting hybridomas under suitable conditions for production of monoclonal antibodies and recovering the produced chimeric mouse-human monoclonal antibodies.

\* \* \* \* \*